United States Patent
Harms et al.

(10) Patent No.: US 8,161,967 B2
(45) Date of Patent: Apr. 24, 2012

(54) BOUGIE DEVICE

(76) Inventors: Stefan Harms, Winnipeg (CA); Chris Christodoulou, Winnipeg (CA); Trevor W. R. Lee, Winnipeg (CA)

(*) Notice: Subject to any disclaimer, the term of this patent is extended or adjusted under 35 U.S.C. 154(b) by 383 days.

(21) Appl. No.: 12/600,169

(22) PCT Filed: May 12, 2008

(86) PCT No.: PCT/CA2008/000885
§ 371 (c)(1),
(2), (4) Date: Nov. 13, 2009

(87) PCT Pub. No.: WO2008/138119
PCT Pub. Date: Nov. 20, 2008

(65) Prior Publication Data
US 2010/0307489 A1  Dec. 9, 2010

Related U.S. Application Data

(60) Provisional application No. 60/917,687, filed on May 14, 2007.

(51) Int. Cl.
*A61M 11/00* (2006.01)

(52) U.S. Cl. .......... 128/200.26; 128/207.15; 128/207.29

(58) Field of Classification Search ............. 128/200.26, 128/207.14, 207.15, 207.29; 606/194
See application file for complete search history.

(56) References Cited

U.S. PATENT DOCUMENTS

| 4,185,639 A | 1/1980 | Linder |
| 5,766,202 A | 6/1998 | Jones et al. |
| 6,146,402 A | 11/2000 | Munoz |

FOREIGN PATENT DOCUMENTS

WO  WO9855170  12/1998

*Primary Examiner* — Steven Douglas
(74) *Attorney, Agent, or Firm* — Ryan W. Dupuis; Kyle R. Satlerthwaite; Ade & Company Inc.

(57) ABSTRACT

A bougie device for guiding insertion of an endotracheal tube into an airway of a person, comprises an elongate body of shape memory and self-lubricating material, for example Teflon™. Accordingly no lubrication is required for insertion into the airway for ease of cleaning and sterilizing for reuse. Also, the amount of curvature of the overall rod as well as an angle of the tip of the rod can be adjusted due to the shape memory characteristics of the body to accommodate a particular patent's airway. The body can also be suitably sized to have vibration transmission characteristics such that a contact with one end of the bougie device with tracheal rings of the patient can be felt by a user.

18 Claims, 3 Drawing Sheets

BOUGIE DEVICE

This application claims priority to U.S. provisional application Ser. No. 60/917,687, filed May 14, 2007.

FIELD OF THE INVENTION

The present invention relates to a bougie device and method of use thereof, and more particularly relates to a bougie device which is suitable for guiding insertion of an endotracheal tube into an airway of a person.

BACKGROUND

Use of a bougie is known for guiding insertion of various instruments into a passageway in a patient's body. Such devices may be formed of rubber, plastic or metal. Known devices generally require lubrication and are not well suited to adjusting the shape thereof to accommodate the different sizes and contours of passageways in different patients which are desired to be accommodated. Certain types of bougies are formed of material, for example latex, where allergies may be a problem.

One type of bougie device is available by Sun-Med™, referred to as the Sun-Med Bougie Introducer™. The device comprises an elongate latex free rod which is packaged to extend generally straight between both ends thereof and accordingly when in a relaxed state, the rod does not fit well with the natural curvature of a person's airway. Furthermore lubrication is required for insertion into the airway of the patient.

SUMMARY OF THE INVENTION

According to one aspect of the invention there is provided a bougie device for guiding insertion of an endotracheal tube into an airway of a person, the device comprising:
an elongate body arranged to be slidably received through the endotracheal tube;
the body comprising polytetrafluoroethylene.

According to a second aspect of the present invention there is provided a bougie device for guiding insertion of an endotracheal tube into an airway of a person, the device comprising:
an elongate body arranged to be slidably received through the endotracheal tube;
the body comprising a shape memory material such that the body is arranged to be bent from a starting orientation into an auxiliary orientation and be substantially retained in the auxiliary orientation.

According to a third aspect of the present invention there is provided a bougie device for guiding insertion of an endotracheal tube into an airway of a person, the device comprising:
an elongate body arranged to be slidably received through the endotracheal tube;
the body comprising a self lubricated material.

By providing a bougie device which is formed of Teflon™, or polytetrafluoroethylene, the resulting bougie device is self lubricated, that is no lubrication is typically required for insertion into an airway passage of a patient. The device is thus easier to clean and easier to sterilize for reuse. Forming the device uniformly of Teflon™ also permits the rod forming the device to be readily reshaped due to shape memory characteristics of the material. The amount of curvature of the overall rod as well as an angle of the tip of the rod can be accordingly adjusted to accommodate a particular patent's airway. When suitably sized to have a diameter, for example in the range of ⅛ of an inch to ¼ of an inch, the Teflon™ rod can accordingly be arranged to have suitable vibration transmission characteristics such that a contact with one end of the bougie device with tracheal rings of the patient can be felt by a user of the device holding the opposing end of the rod.

The body is preferably arranged to have vibratory transmission properties such that contact between one end of the body with tracheal rings in the airway of the person can be felt by a user contacting the opposing end of the body.

Preferably the body consists of a uniform material.

When a main portion of the body is curved along a length thereof in a first direction, one or both end portions of the body may be bent in relation to the main portion in the first direction.

The body may be demarcated at prescribed distances from an insertion end of the body corresponding to a degree of insertion into the airway of the patient.

According to another aspect of the present invention there is provided a method of guiding insertion of an endotracheal tube into an airway of a person, the method comprising:
providing a bougie device comprising an elongate body;
arranging the body to comprise polytetrafluoroethylene;
inserting the bougie device into the airway;
positioning the endotracheal tube over the elongate body of the bougie device such that the elongate body is slidably received in the endotracheal tube; and
removing the bougie device.

According to yet another aspect of the present invention there is provided a method of guiding insertion of an endotracheal tube into an airway of a person, the method comprising:
providing a bougie device comprising an elongate body;
arranging the body to comprise a shape memory material such that the body is arranged to be bent from a starting orientation into an auxiliary orientation and be substantially retained in the auxiliary orientation;
inserting the bougie device into the airway;
positioning the endotracheal tube over the elongate body of the bougie device such that the elongate body is slidably received in the endotracheal tube; and
removing the bougie device.

According to a further aspect of the present invention there is provided a method of guiding insertion of an endotracheal tube into an airway of a person, the method comprising:
providing a bougie device comprising an elongate body;
arranging the body to comprise a self lubricated material;
inserting the bougie device into the airway;
positioning the endotracheal tube over the elongate body of the bougie device such that the elongate body is slidably received in the endotracheal tube; and
removing the bougie device.

The method may further include storing the body in a package which maintains the body in a curved position.

The body may be formed by cutting the body from strand material wound on a roll such that the body is inherently curved.

The body may be arranged to have vibratory transmission properties such that contact between one end of the body with tracheal rings in the airway of the person can be felt by a user contacting the opposing end of the body.

One embodiment of the invention will now be described in conjunction with the accompanying drawings in which:

BRIEF DESCRIPTION OF THE DRAWINGS

In the drawings like characters of reference indicate corresponding parts in the different figures.

DETAILED DESCRIPTION

Figure 1:
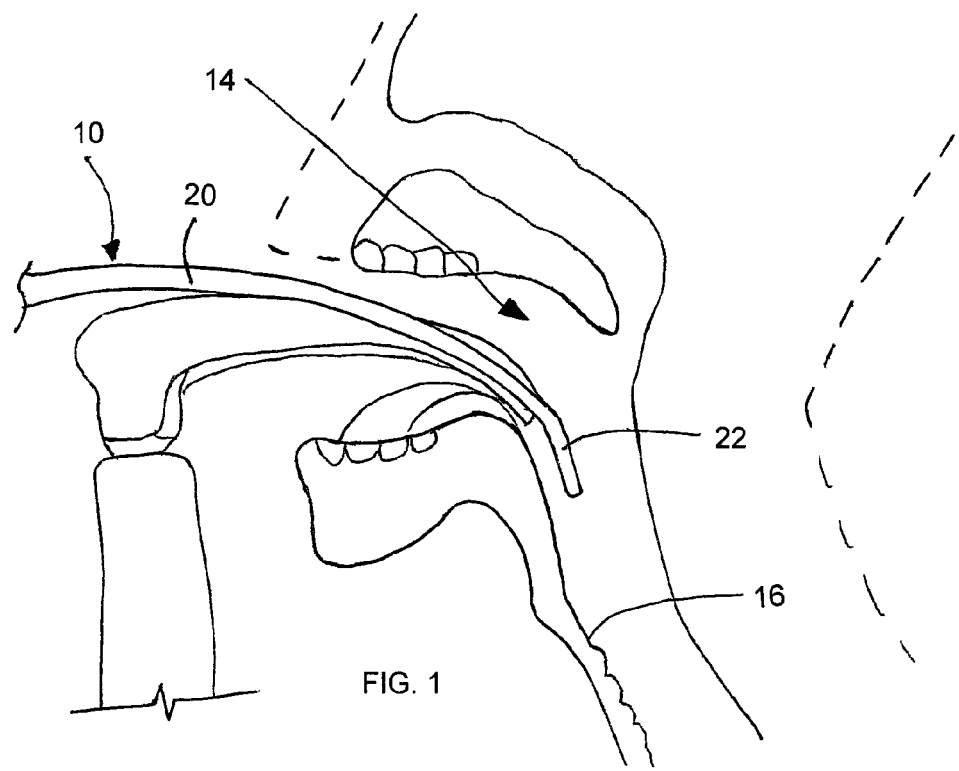
FIG. 1 is a schematic illustration of a human airway in which a laryngoscope is used to assist insertion of the bougie device into the trachea.

Referring to the accompanying figures there is illustrated a bougie device generally indicated by reference numeral 10. The device 10 is particularly suited for guiding insertion of an instrument into a passageway in a patient. The device described herein is particularly suited for guiding an endotracheal tube 12 for insertion into the airway 14 of a patient so that an end of the endotracheal tube is positioned at the tracheal rings 16 in the trachea of the patient.

The device 10 generally comprises a rod of uniform material consisting of Teflon™, or polytetrafluoroethylene. In the illustrated embodiment, the rod is in the order of two to three feet in length and has a diameter of 3/16 of an inch when used on adults or 1/8 of an inch when used on children. The ends of the rod are rounded.

Forming the device of Teflon™ is particularly useful as the resulting bougie is self lubricated, in that it requires little or no lubrication for insertion into a patient's airway. Furthermore the material forming the bougie device is a shape memory material, that is when its orientation is manually bent and varied, the material can remain in the varied orientation so that the particular shape and configuration of the rod can be readily and manually adjusted by a user according to a particular patient's needs.

In the illustrated embodiment the bougie device 10 comprises a rod having a main portion 20 which is generally curved to form the general circumference of a circle when in a relaxed state. End portions 22 are formed at each of the two opposing ends of the main portion 20 to extend therefrom in the order of two to three centimetres. The end portions 22 are joined with the main portion at a bend such that each end portion is inclined, for example in the order of thirty degrees, in relation to the main portion in the direction of curvature of the main portion 20. The amount of bent inclination of the end portions relative to the main portion can be readily and manually adjusted by the user due to the shape memory properties of the material forming the bougie device.

Figure 2:
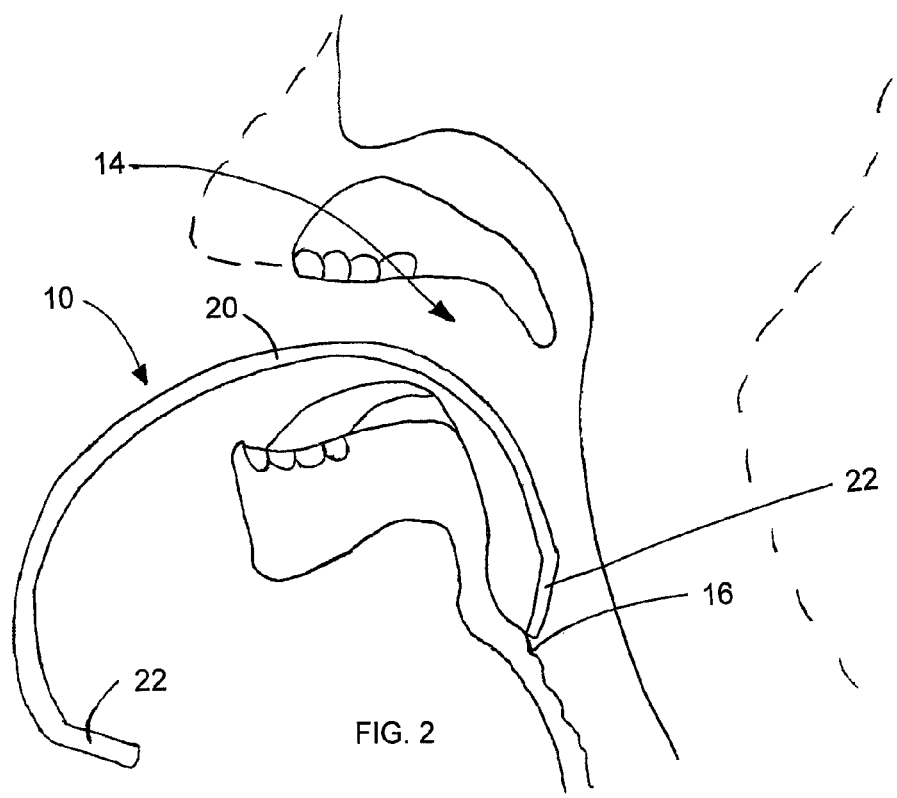
FIG. 2 shows the bougie device inserted into the patient's trachea in contact with the tracheal rings.
Figure 3:
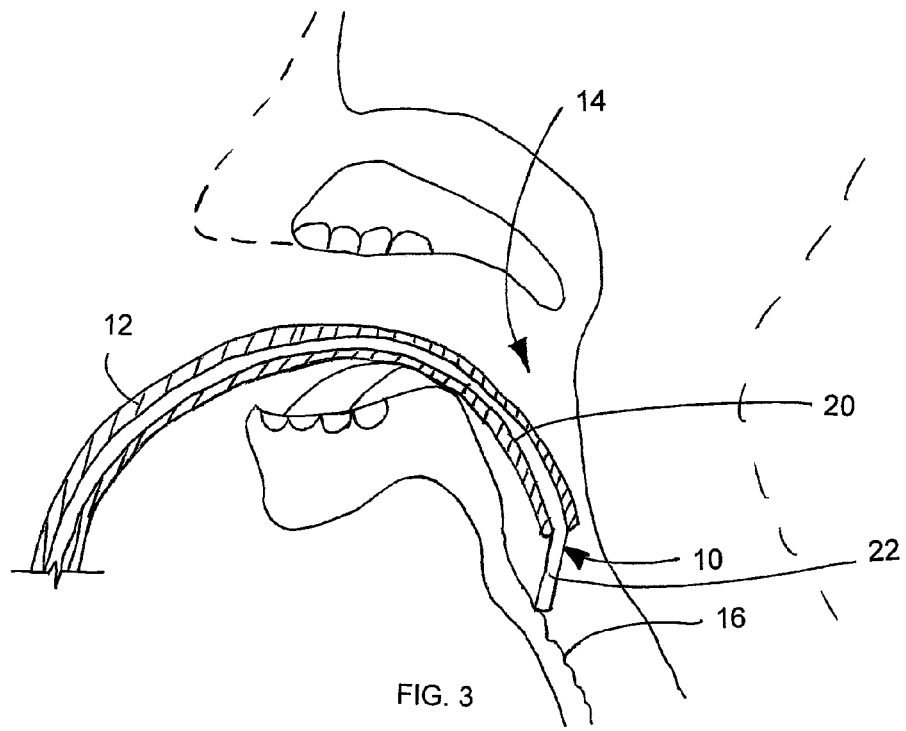
FIG. 3 is a schematic illustration of an endotracheal tube which has been inserted over the bougie device which acts to guide the tube into the patient's trachea.

In use, when it is desired to insert an endotracheal tube into an airway of a patient, a laryngoscope is first used and inserted into the patient's airway to assist in moving some of the patient's soft tissues out of the way of the entry into the airway. The bougie device 10 can then be inserted into the airway with the curve of the main portion being oriented to generally follow the curvature of the airway of the person. Accordingly the bent end portion at the inserted end of the bougie device is arranged to be oriented to be bent downwardly and forwardly in relation to the airway. The tip is thus suitably arranged for engaging the tracheal rings 16 of the patient as shown in FIG. 2. The material forming the bougie device and the dimensions thereof are arranged so that the resulting bougie device has suitable vibration transmission properties arranged such that a contact of the end portion of the bougie device along the tracheal rings causes vibrations to be sensed by a user contacting the opposing end of the bougie device.

Figure 4:
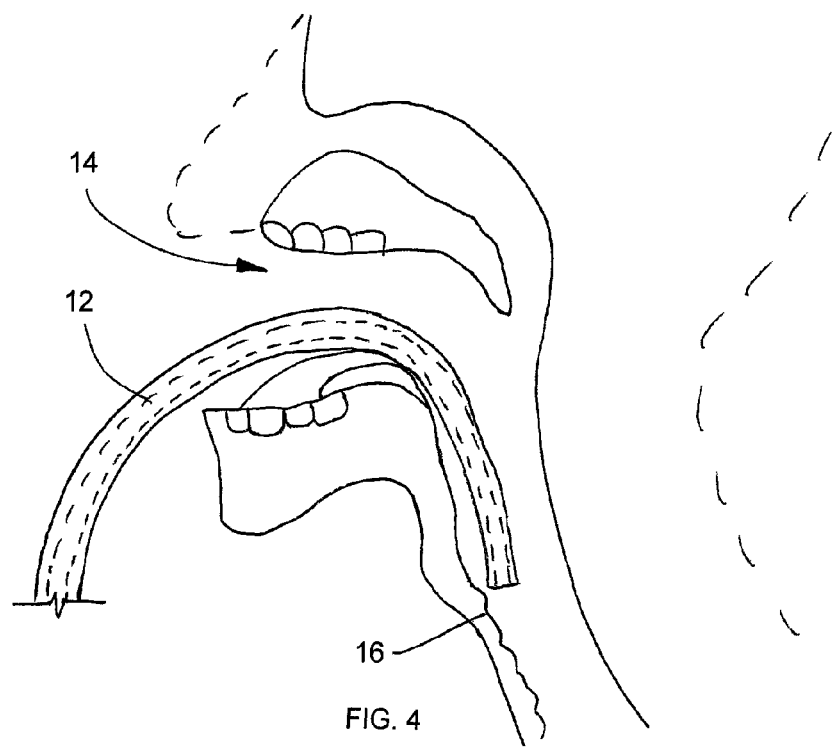
FIG. 4 illustrates the resulting position of the endotracheal tube after removal of the bougie device.
Figure 5:
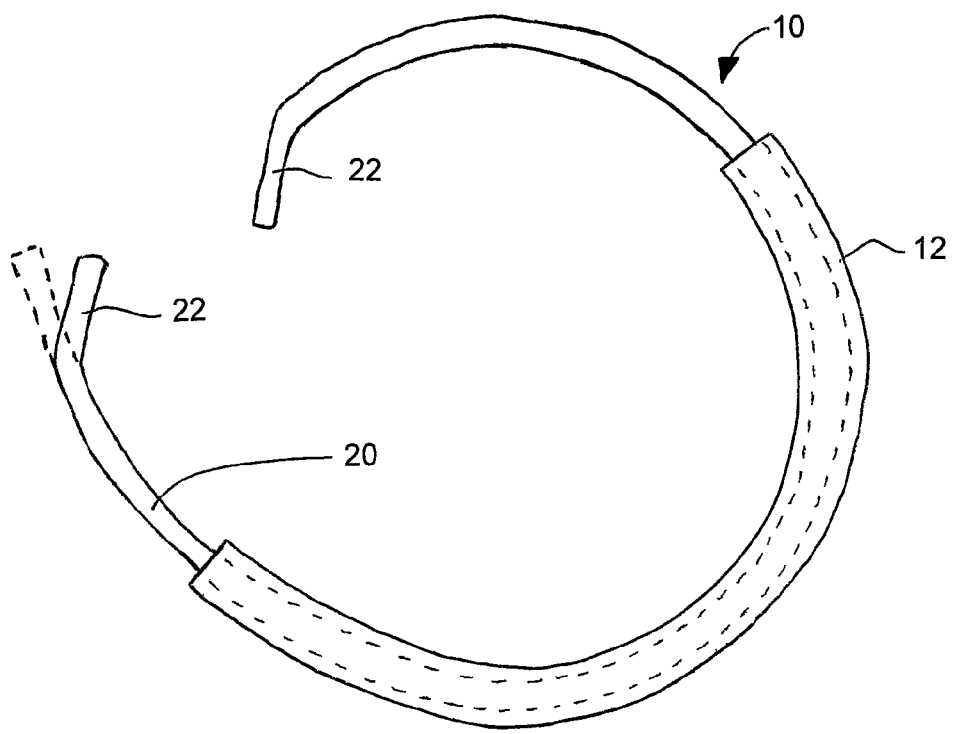
FIG. 5 is a schematic illustration of the bougie device inserted through an endotracheal tube.
Figure 6:
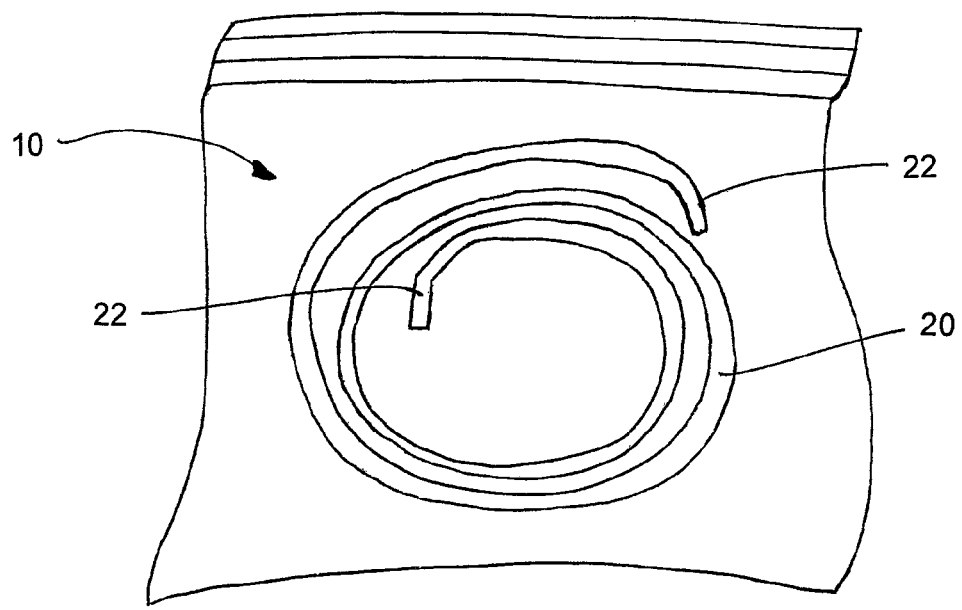
FIG. 6 is a schematic illustration of the bougie device in a suitable package for maintaining a curvature of the device.

Once the bougie device 10 has been located relative to the patient's trachea, the endotracheal tube 12 can be inserted over the bougie device as the bougie device is suitably dimensioned to be slidably received through the tube 12. Once the tube is fully inserted over the inserted end of the bougie device 10, the device 10 can be removed leaving only the endotracheal tube 12 positioned in the airway to terminate near the tracheal rings 16 in the trachea as shown in FIG. 4.

The bougie device 10 has been found to be economically manufactured by cutting two to three foot lengths of suitable diameter Teflon™ strand material from a roll so that once the appropriate length has been cut from the strand material the device has an inherent curvature already which is suitable for forming the curvature of the main portion 20 of the device. The bougie device is then preferably packaged in a suitable package 24 which maintains the main portion 20 in a wound up or curved state to maintain the curvature thereof.

The bougie device described herein is a unique Teflon™ introducer which aids in endotracheal incubation. Teflon™ has the advantages of being latex free, being easy to disinfect, being flexible but firm, and does not require lubrication when placed within the lumen of an endotracheal tube. The device can be formed to have a natural curvature which is easy to insert into the oropharynx and is malleable enough for the user to fashion a curved tip two to three centimetres from the distal end of the device. This tip can be changed according to the desires of the user due to the shape memory properties of the material. The resulting bougie device 10 is compact, lightweight and easy to place in a clinic coat pocket for example so that a clinician can have a device available at all times. Because the bougie device described herein is relatively flexible compared to other devices, it offers a greater degree of sensitivity when the tip contacts the tracheal rings of the patient and the vibrations of the tip of the device moving over the rings can be easily felt.

The device 10 can be made of various lengths and diameters of white extruded virgin Teflon™ rods, the most favourable being 3/16 of an inch in diameter and two feet in length for use in the adult patient. A three foot length device can be used to facilitate double lumen endotracheal tube intubation. A paediatric version of the device 10 can be made from 1/8 inch diameter, one foot extruded virgin Teflon™ rods. Both ends of the device are machined in a domed shaped fashion to prevent trauma to the airway of the patient. Either end can thus be used for insertion.

In addition to the device being usable to facilitate difficult, or blind single, or double lumen endotracheal tube intubation of an adult or paediatric patient, the device may also be used for endotracheal tube exchange.

The Teflon™ rods forming the bougie device can be disinfected with glutaraldehyde, or washing in a washer disinfector, according to usual institutional practices. The device 10 may also be sterilized with ethylene oxide or autoclaved according to usual institutional practices.

The device can also be scored or otherwise demarcated at prescribed distances from an insertion end of the body to judge distance from the tip or insertion end at 10, 20 or 30 centimetres so as to judge the degree of insertion of the device into the airway of a patient.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. A method of guiding insertion of an endotracheal tube into an airway of a person, the method comprising:
   providing a bougie device comprising an elongate body which is formed of polytetrafluoroethylene and which is cut from strand material wound on a roll such that the body is inherently curved and such that the body has vibratory transmission properties such that contact between one end of the body with tracheal rings in the airway of the person can be felt by a user contacting the opposing end of the body;
   inserting the bougie device into the airway;
   positioning the endotracheal tube over the elongate body of the bougie device such that the elongate body is slidably received in the endotracheal tube; and
   removing the bougie device.

2. The method according to claim 1 wherein the body comprises a shape memory material such that the body is arranged to be bent from a starting orientation into an auxiliary orientation and be substantially retained in the auxiliary orientation.

3. The method according to claim 1 wherein the body comprises a self lubricated material.

4. The method according to claim 1 including storing the body in a package which maintains the body in a curved position.

5. The method according to claim 1 wherein the body is formed of a uniform material.

6. The method according to claim 1 wherein a main portion of the body is curved along a length thereof in a first direction and at least one end portion of the body is bent in relation to the main portion in the first direction.

7. The method according to claim 6 wherein said at least one end portion comprises a shape memory material such that a bent angle of the end portion relative to the main portion of the body is arranged to be manually adjusted from a starting orientation into an auxiliary orientation and be substantially retained in the auxiliary orientation.

8. The method according to claim 6 wherein said at least one end portion comprises two end portions at opposing ends of the main portion of the body, both end portions being bent in relation to the main portion in the first direction.

9. The method according to claim 1 wherein the body is demarcated at prescribed distances from an insertion end of the body corresponding to degrees of insertion into the airway of the patient.

10. A method of forming a bougie device for use in guiding insertion of an endotracheal tube into an airway of a person by inserting the bougie device into the airway, positioning the endotracheal tube over the elongate body of the bougie device, and removing of the bougie device, the method of forming the bougie device comprising:
    forming a body of the bougie device to be elongate by cutting the body from strand polytetrafluoroethylene material wound on a roll such that:
    the body is inherently curved; and
    the body has vibratory transmission properties such that contact between one end of the body with tracheal rings in the airway of the person can be felt by a user contacting the opposing end of the body.

11. The method according to claim 10 including arranging the body to comprise a shape memory material such that the body is arranged to be bent from a starting orientation into an auxiliary orientation and be substantially retained in the auxiliary orientation.

12. The method according to claim 10 including arranging the body to comprise self lubricated material.

13. The method according to claim 10 including storing the body in a package which maintains the body in a curved position.

14. The method according to claim 10 including forming the body of a uniform material.

15. The method according to claim 10 including arranging a main portion of the body to be curved along a length thereof in a first direction and arranging at least one end portion of the body to be bent in relation to the main portion in the first direction.

16. The method according to claim 15 including arranging said at least one end portion to comprise a shape memory material such that a bent angle of the end portion relative to the main portion of the body is arranged to be manually adjusted from a starting orientation into an auxiliary orientation and be substantially retained in the auxiliary orientation.

17. The method according to claim 15 wherein said at least one end portion comprises two end portions at opposing ends of the main portion of the body in which both end portions are bent in relation to the main portion in the first direction.

18. The method according to claim 10 demarcating the body at prescribed distances from an insertion end of the body corresponding to a degree of insertion into the airway of the patient.

* * * * *